United States Patent
Nagai et al.

(10) Patent No.: US 7,767,969 B2
(45) Date of Patent: Aug. 3, 2010

(54) METHOD AND APPARATUS FOR MEASURING SPECTROSCOPIC ABSORBANCE

(75) Inventors: Kiyoshi Nagai, Nagasaki (JP); Harumi Shibata, Nagasaki (JP); Sayaka Hamaguchi, Nagasaki (JP)

(73) Assignee: Sumco Techxiv Corporation, Nagasaki (JP)

( * ) Notice: Subject to any disclaimer, the term of this patent is extended or adjusted under 35 U.S.C. 154(b) by 37 days.

(21) Appl. No.: 12/319,332

(22) Filed: Jan. 6, 2009

(65) Prior Publication Data

US 2009/0173884 A1 Jul. 9, 2009

(30) Foreign Application Priority Data

Jan. 8, 2008 (JP) ............... 2008-001677

(51) Int. Cl.
*G01J 5/06* (2006.01)
(52) U.S. Cl. ..................................... 250/340
(58) Field of Classification Search .......... 250/340, 250/343; 600/322
See application file for complete search history.

(56) References Cited

U.S. PATENT DOCUMENTS

2008/0009748 A1* 1/2008 Gratton et al. ............... 600/475

FOREIGN PATENT DOCUMENTS

| JP | 06-194310 | 7/1994 |
|---|---|---|
| JP | 2007-018624 | 1/2007 |

\* cited by examiner

*Primary Examiner*—David P Porta
*Assistant Examiner*—Mark R Gaworecki
(74) *Attorney, Agent, or Firm*—Edwards Angell Palmer & Dodge LLP; Jeffrey D. Hsi

(57) ABSTRACT

An object of the present invention is to provide a spectroscopic method and an apparatus which can measure a trace element accurately with high sensitivity. In order to achieve this object, for example, in Fourier transformation infrared spectroscopy (FT-IR), a reference spectrum and a measurement spectrum including an impurity spectrum are measured in order to obtain a differential spectrum comprising the impurity spectrum and a flat baseline, correction including a frequency shift of the reference spectrum before calculating a differential spectrum, is performed on the reference spectrum. This makes it possible to remove baseline deformation due to phonon absorbance of silicon included in the conventional differential spectrum, and to obtain an infrared absorption spectrum of the substitutional carbon with high accuracy and high sensitivity.

7 Claims, 7 Drawing Sheets

( Prior Art )

METHOD AND APPARATUS FOR MEASURING SPECTROSCOPIC ABSORBANCE

This application is based on and claims the benefit of priority from Japanese Patent Application No. 2008-001677, filed on 8 Jan. 2008, the content of which is incorporated herein by reference.

BACKGROUND OF THE INVENTION

1. Field of the Invention

The present invention relates to a method of measuring spectroscopic absorbance such as Fourier transform infrared spectroscopy (FT-IR), and to an apparatus for measuring spectroscopic absorbance embodying the method.

2. Related Art

Conventionally, in the quality evaluation of a semiconductor producing process, FT-IR has been used to measure the concentration of substitutional carbon that is an impurity in a silicon single crystal. Specifically, a technique is known, in which differential spectroscopy is used to obtain an infrared absorption spectrum of substitutional carbon that is an impurity included in a measurement target (sample), by means of subtraction factor correction by subtracting an infrared absorption spectrum, which has been obtained from a substantially carbon-free silicon single crystal (reference), from an infrared absorption spectrum which has been obtained from a silicon single crystal that is the measurement target (sample), as disclosed in a Japanese Unexamined Patent Application, First Publication No. H06-194310 (Patent Document 1). The subtraction factor correction is used in order to remove the strong absorbance due to phonon absorbance of the silicon that is present overlapping with a minute spectrum of the substitutional carbon.

FIG. 7 is a diagram showing an example of a differential infrared absorption spectrum of substitutional carbon which has been corrected with a subtraction factor of the prior art. In this prior art, the range of the absorption peak of the substitutional carbon included in a difference spectrum is expediently set as the range of wave numbers from 595 to 615 cm$^{-1}$ and a straight line passing both ends of this range is set as a base line 122, thereby obtaining a signal strength.

In addition, another prior art is known, which relates to a calibration curve correction method in near infrared spectroscopy. In the calibration curve correction method, a calibration curve created before the correction is applied to the corrected measurement spectrum. In this case, wave number shift correction is performed on the measurement spectrum to shift its wave number, and scale correction is performed for the wave number-shifted measurement spectrum, thereby applying the calibration curve to the corrected spectrum, as disclosed in a Japanese Unexamined Patent Application, First Publication No. 2007-18624 (Patent Document 2).

SUMMARY OF THE INVENTION

In the differential spectroscopy of Patent Document 1, a distortion 121 remains around the wave number 630 cm$^{-1}$ as shown in FIG. 7. The inventors consider that the position of this distortion corresponds to the steep region of the strong phonon absorbance, and the distortion is caused by shift in the transverse axis to a minute extent between the reference spectrum and the sample spectrum. In this way, in the method of Patent Document 1 using merely the differential spectrum, strong absorbance due to phonon absorbance exists as a background. Accordingly, in cases where a wave number shift exists between the reference spectrum and the sample spectrum even to a minute extent, it is not possible to sufficiently remove the influence of phonon absorbance from the differential spectrum. As a result, a sufficiently satisfactory baseline cannot be obtained, and the baseline is full of unevenness, leading to a problem that it is impossible to obtain an exact peak height of the impurity concentration of interest.

Moreover, the use of the wave number shift in Patent Document 2 aims to correct a calibration curve being changed due to maintenance of apparatus, and there is no disclosure or suggestion regarding the correct capturing of a minute absorption spectrum in a region overlapping with other strong absorbance by the differential spectroscopy.

The inventors of the present invention have made every effort and studied to solve the problem of the aforementioned prior art, particularly of Patent Document 1, and have found that the baseline deviation of the differential spectrum is caused by a minute frequency shift due to the different conditions of apparatus or samples when measuring the spectrum of the sample and the reference. The inventors have found that it is possible to obtain a satisfactory baseline and an absorption peak, in which the influence of the background has been effectively removed, by estimating a minute frequency shift amount with the least squares method, the amount being necessary to obtain a satisfactory differential spectrum, and have completed the present invention. Specifically, the present invention provides the following means for solving the problem.

According to a first aspect of the present invention, a method of measuring spectroscopic absorbance is provided, in differential spectroscopy, for obtaining only a spectroscopic absorption spectrum of a measurement component from a sample spectrum of a measurement sample and from a reference spectrum of a reference sample, the sample spectrum having spectroscopic absorbance of the measurement component and a background component in a frequency domain overlapping with the spectroscopic absorbance of the measurement component, and the reference spectrum substantially not including the measurement component but having the spectroscopic absorbance of the background component, in which, when the differential spectrum is obtained, correction is performed including a frequency shift to any one of the sample spectrum or the reference spectrum in order to remove the spectroscopic absorbance of the background component.

According to a second aspect of the present invention, a method of measuring spectroscopic absorbance is provided, in differential spectroscopy, for obtaining only a spectroscopic absorption spectrum of a measurement component from a sample spectrum of a measurement sample and from a reference spectrum of a reference sample, the sample spectrum having spectroscopic absorbance of the measurement component and a background component in a frequency domain overlapping with the spectroscopic absorbance of the measurement component, and the reference spectrum substantially not including the measurement component but having the spectroscopic absorbance of the background component, in which, when the differential spectrum is obtained, correction is performed including a frequency shift to any one of the sample spectrum or the reference spectrum in order to substantially flatten the baseline.

In the first or second aspect, an amount of the frequency shift may not be greater than frequency resolution of the spectroscopic absorbance measurement.

According to a third aspect of the present invention, the method of measuring spectroscopic absorbance as recited in any one of the first to the third aspects is provided, in which the method of measuring spectroscopic absorbance is FT-IR (Fourier transformation infrared spectroscopy), the measurement component is an impurity in a silicon single crystal, and concentration of the impurity is determined from a spectroscopic absorbance peak height of the measurement component in the differential spectrum.

In the third aspect, the impurity may be substitutional carbon.

According to a fourth aspect of the present invention, the method of measuring spectroscopic absorbance as recited in any one of the first to third aspects is provided, in which a spectroscopic absorbance peak due to the substitutional carbon in the differential spectrum is considered a signal, and a standard deviation of the differential absorbance in the wave number domain around the spectroscopic absorbance peak is considered noise, thereby allowing the calculation a signal-to-noise ratio of the infrared absorption differential spectrum due to the substitutional carbon.

According to a fifth aspect of the present invention, a computer program is provided for causing a computer to perform the steps of, storing a sample spectrum having spectroscopic absorbance of the measurement component and a background component in a frequency domain overlapping with the spectroscopic absorbance of the measurement component, storing a reference spectrum substantially not including the measurement component but having the spectroscopic absorbance of the background component, removing the spectroscopic absorbance of the background component by correction including a frequency shift to any one of the sample spectrum or the reference spectrum, and calculating a correction factor for flattening a baseline of the spectroscopic absorbance of the measurement component, and calculating a differential spectrum of the sample spectrum and the reference spectrum by using the correction factor.

According to a sixth aspect of the present invention, a computer-readable recording medium is provided on which the computer program as recited in the seventh aspect is recorded.

According to a seventh aspect of the present invention, an apparatus for measuring spectroscopic absorbance is provided, the apparatus comprising, a first device configured to store a sample spectrum having spectroscopic absorbance of the measurement component and a background component in a frequency domain overlapping with the spectroscopic absorbance of the measurement component, a second device configured to store a reference spectrum substantially not including the measurement component but having the spectroscopic absorbance of the background component, and a device configured to calculate a differential spectrum of the sample spectrum and the reference spectrum, in which the device configured to calculate the differential spectrum performs correction including a frequency shift to any one of the sample spectrum or the reference spectrum in order to remove the spectroscopic absorbance of the background component.

According to the present invention, in cases where differential spectroscopy is used in spectroscopic absorbance measurement such as FT-IR, it is possible to effectively remove background influence, and to obtain a satisfactory baseline, thereby making it possible to enhance detection sensitivity as compared to conventional methods.

This method is extremely effective in determining impurity concentration in a silicon single crystal or the like.

DETAILED DESCRIPTION OF THE INVENTION

One embodiment of the present invention will hereinafter be described in detail. It should be noted that this is merely an example, and the technical scope of the present invention is not limited thereto.

Apparatus for Measuring Spectroscopic Absorbance

Figure 2:
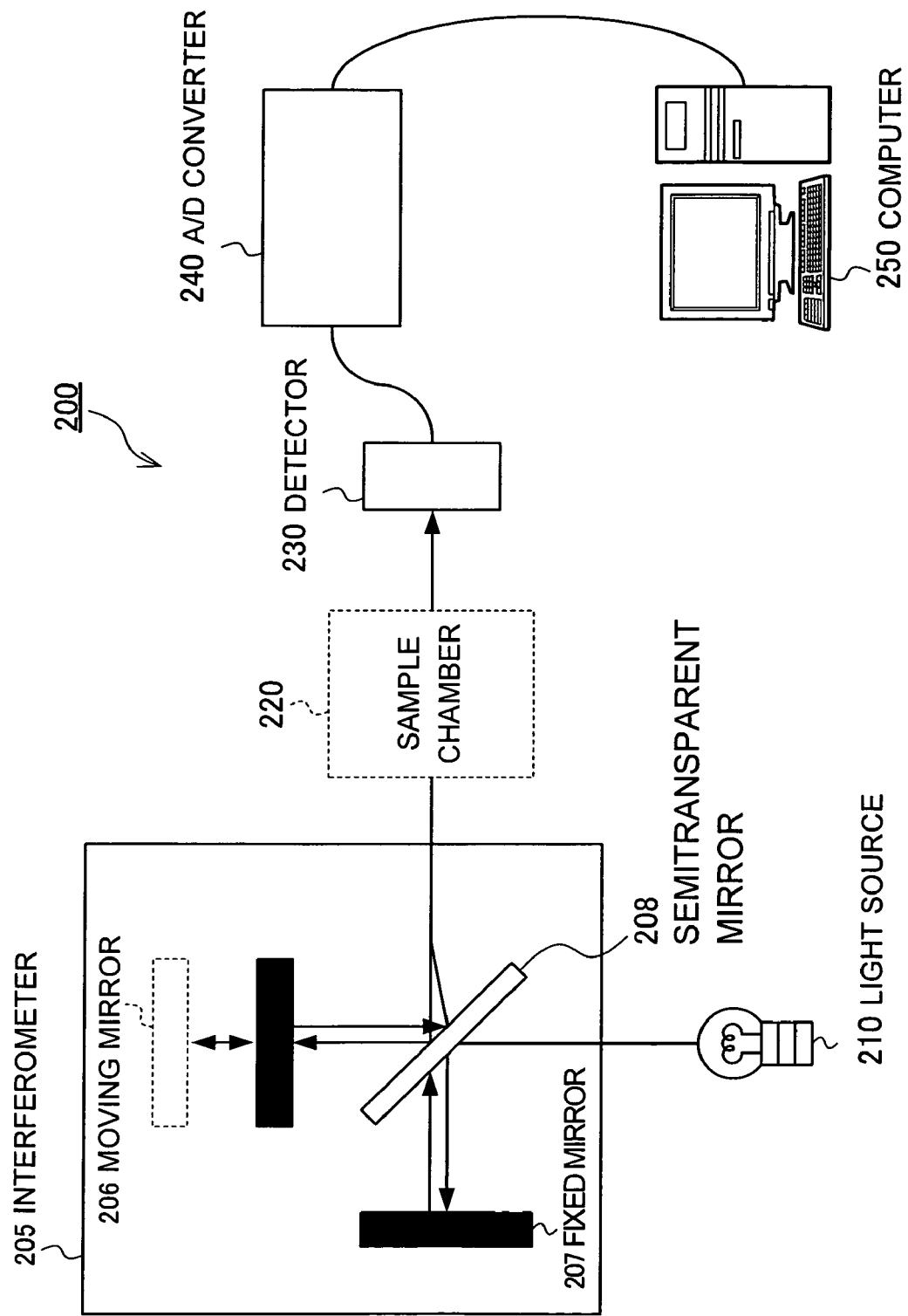
FIG. 2 is a diagram showing a configuration of an FT-IR apparatus which is one embodiment of the present invention.

FIG. 2 shows a configuration of an FT-IR apparatus 200, which is an example of the apparatus for measuring spectroscopic absorbance of the present invention. The FT-IR apparatus 200 includes an interferometer 205, a moving mirror 206, a fixed mirror 207, a semitransparent mirror 208, a light source 210, a sample chamber 220, a detector 230, an A/D converter 240, and a computer 250. The interference light generated by the light source 210 and the interferometer 205 passes the sample chamber 220, arrives at the detector 230, and is converted into an electrical signal by detecting the signal strength. The electrical signal undergoes digital conversion at the A/D converter 240 and a computation process such as Fourier transformation by use of the computer 250. The obtained information is output as distribution of the infrared absorption intensity in the wave number domain.

It should be noted that the means for measuring spectroscopic absorbance, to which the present invention is applied, is not limited to FT-IR, but includes conventionally well-known means for measuring spectroscopic absorbance. For example, it is a matter of course that the present invention is also applied to obtaining an infrared absorption spectrum as an output from a detector by sweeping a wave number domain. Moreover, frequency domain is not particularly limited, and the present invention is applied to any frequency domain such as ultraviolet, visible, near infrared, infrared and far infrared. Above all, for the determination of an impurity in a silicon single crystal to be described later, it is preferable to use FT-IR in view of the target impurity and the measurement sensitivity. Moreover, for example, the infrared spectroscopy apparatus of the present invention may be incorporated into a production line of a silicon single crystal to be used as automatic quality evaluating means or automatic testing means.

Measurement Sample and Reference Material

A measurement sample to be used for the present invention is not particularly limited as long as the sample contains a measurement component having spectroscopic absorbance and a background component that has spectroscopic absorbance in a frequency domain that overlaps with the spectroscopic absorbance of the measurement component. For example, taking a silicon single crystal as an example, a single crystal of either the Czochralski method (CZ method) silicon single crystal or the floating zone method (FZ method) silicon single crystal is applicable. In this case, the measurement component is a so-called impurity component, and is specifically carbon or oxygen. Specifically, the concentration of the impurity component can not be more than 1 ppma (parts per million atoms), but is not particularly limited. On the other hand, the background component arises from phonon absorbance of the silicon. Specifically, the infrared absorption spectrum due to phonon absorbance is in the range of 565 to 645 cm$^{-1}$, and overlaps with the infrared absorption spectrum of the substitutional carbon at around 605 cm$^{-1}$.

A reference sample to be used for the present invention is not particularly limited as long as the sample substantially does not contain the measurement component but contains the background component. In cases where the measurement sample is a silicon single crystal that contains the impurity, it is preferable that the reference sample be a silicon single crystal which substantially does not contain the impurity, and which is made by a manufacturing method that is the same as that of the measurement sample. It should be noted that "substantially does not contain the impurity" means that the impurity is not greater than the detection limit or that a carbon peak cannot be detected.

It should be pointed out, as a characteristic of the present invention, that the measurement component of the measurement sample can be detected with high sensitivity. Specifically, as described later, taking carbon concentration in the silicon single crystal as an example, the lower detection limit thereof is approximately $3 \times 10^{14}$ a/cm$^3$ (the number of atoms per unit cubic centimeter), and this is 15 times more sensitive compared to the quantitative determination method of the substitutional carbon which is approximately $4.5 \times 10^{15}$ a/cm$^3$ as described in Patent Document 1. Conventionally, it has been extremely difficult to detect such a low carbon concentration with FT-IR.

Frequency Shift

The present invention is characterized in that an optimal frequency shift amount is obtained for either the sample spectrum or the reference spectrum to obtain a differential spectrum, in order to remove by subtracting the spectroscopic absorbance of the background component in the sample and the reference spectrum and to flatten the baseline of the differential spectrum. Minute wave number deviation arises between the sample spectrum and the reference spectrum due to influences such as the instability of the measurement equipment and the temperature fluctuation of the measurement sample itself. In this case, baseline deviation arises in the differential spectrum in the wave number domain where rapid change in phonon absorption is present. The spectroscopic absorbance measurement method of the present invention aims to remove the baseline deviation by numerical calculation of the wave number shift corresponding to the baseline deviation.

A frequency shift amount that provides a satisfactory baseline can take either a plus or minus value, and is often a minute frequency shift amount which is not greater than the frequency resolution of the measuring means. Specifically, in cases of measuring carbon concentration in the silicon single crystal, there are many shifts in a range of wave numbers from 0.01 cm$^{-1}$ to 0.03 cm$^{-1}$. Numerical values of the specific wave number shifts will be described later with examples.

The range of wave numbers of the baseline data treated with the least squares method suffices to be included in the range of wave numbers from 565 to 645 cm$^{-1}$, preferably in the range of wave numbers from 565 to 590 cm$^{-1}$ or in the range of wave numbers from 620 to 645 cm$^{-1}$, more preferably in the range of wave numbers from 570 to 585 cm$^{-1}$ or in the range of wave numbers from 625 to 640 cm$^{-1}$. The range of wave numbers that are used to the calculation of the signal-to-noise ratio can be appropriately set from the aforementioned ranges.

It is preferable that a wave number shift amount be calculated with the least squares method in which the wave number shift amount is considered to the unknown variable. This point will also be described later in detail with specific examples. Other unknown variable may appropriately include baseline offset of first or second order polynomials as a function of the wave number. The unknown variables including the wave number shift amount are calculated by using numerical values included in the baseline regions of the measurement spectrum and the reference spectrum.

Specific Example of Frequency Shift Correction

Figure 1:
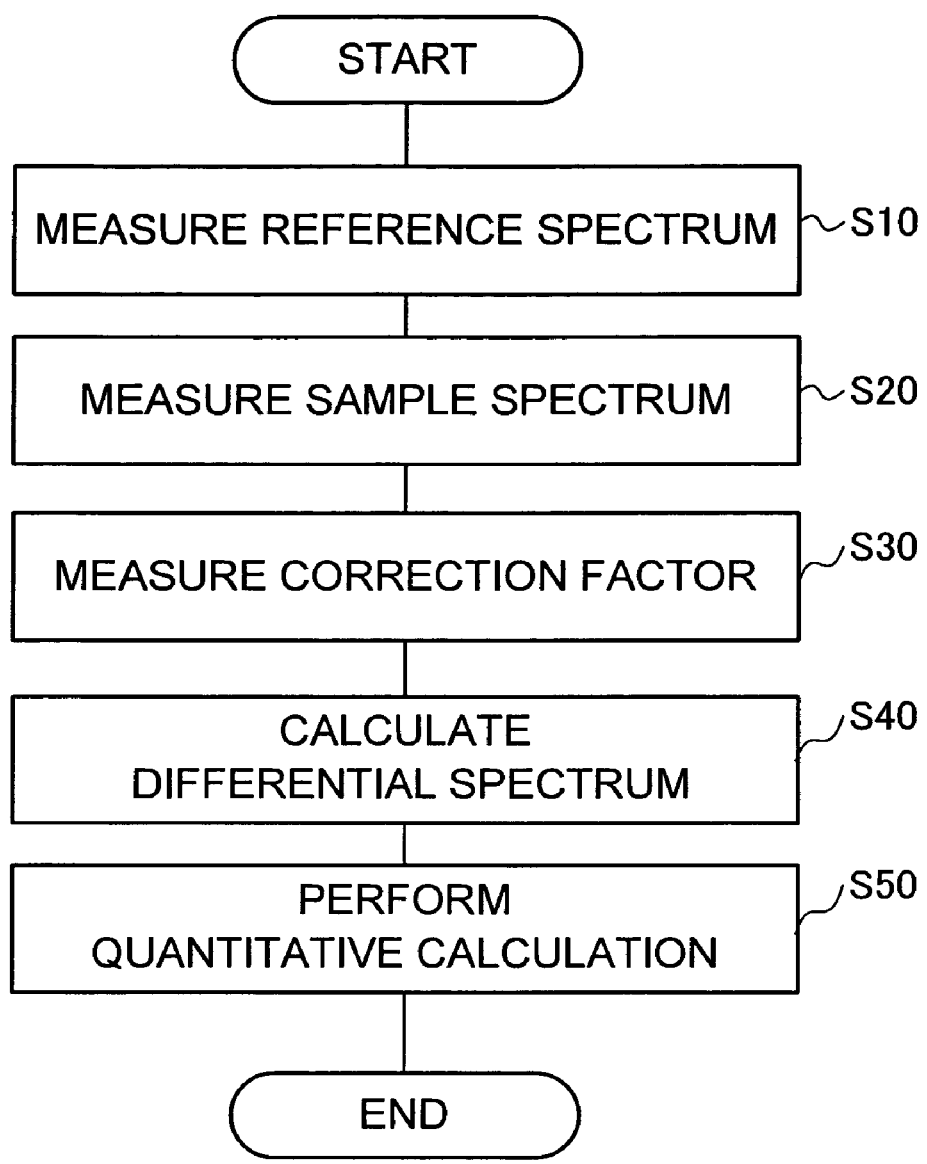
FIG. 1 is a flow diagram showing the procedure of correcting a wave number shift amount and a baseline in the infrared spectroscopy differential spectrum measurement, which is one embodiment of the present invention.

FIG. 1 is a flow diagram showing the procedure steps of obtaining a wave number shift amount and correcting a baseline in the infrared spectroscopy differential spectrum measurement in one embodiment of the present invention, in which the measurement of carbon concentration, which is an impurity in the silicon single crystal, is taken as an example. Moreover, the configuration included in the FT-IR apparatus described with reference to FIG. 2 is referred to in order to explain the flow diagram. It should be noted that wave numbers are used in illustrating the following steps in infrared spectroscopy, but other forms of spectroscopy, in which wavelength or frequency is used, a way similar to the infrared spectroscopy.

At first, at Step (S10) for measuring a reference spectrum, the sample chamber 220 includes a reference sample (not shown) that contains components other than the objective components for quantitative determination. The FT-IR apparatus 200 obtains infrared absorption spectroscopy data (data R) of the reference sample placed in the sample chamber 220, and appropriately stores the data using the computer 250. The infrared absorption spectroscopy data (data R) of the reference sample is expressed with the next equation;

$$A_R(x_k) \quad (1)$$

where $x_k$ is a wave number, and $A_R(x_k)$ is an absorbance value at the wave number $x_k$.

Similarly, at Step (S20) for measuring a sample spectrum, the sample chamber 220 includes a measurement sample (not shown) that is composed of components for the purpose of quantitative determination. The FT-IR apparatus 200 obtains infrared absorption spectroscopy data (data S) of the measurement sample placed in the sample chamber 220, and appropriately stores the data using the computer 250. The infrared absorption spectroscopy data (data S) of the measurement sample is expressed with the following equation;

$$A_S(x_k) \quad (2)$$

where $A_S(x_k)$ is an absorbance value at the wave number $x_k$.

Subsequently, in order to determine the wave number shift amount, the following equation exemplified;

$$A_P(x_k) = a_1 A_R(x_k - a_2) + a_3 + a_4 x_k \quad (3)$$

where $A_P(x_k)$ is a model function of the corrected reference spectrum;

$a_1$ is a, so called, "subtraction factor" for correcting the amplitude difference between the reference spectrum and the sample spectrum;

$a_2$ is a shift amount [cm$^{-1}$] for correcting the wave number shift;

$a_3$ is a zero-order baseline offset; and $a_4$ is a first-order baseline offset.

The model function $A_P(x_k)$ specifically aims to approximate the reference spectrum $A_R(x_k)$ to the sample spectrum $A_S(x_k)$, and more specifically aims to remove distortion around 630 cm$^{-1}$ due to lattice vibration of the silicon single crystal present in the differential spectrum. For such purposes, the model function $A_P(x_k)$ is not limited to Equation 3 but can be appropriately formulated, as long as the shift amount $a_2$ for the wave number shift correction is included.

At correction factor calculation step (S30), a residual square-sum is defined by using the following equation;

$$D = \sum_{x_k \in Q} \{A_S(x_k) - A_P(x_k)\}^2 \quad (4)$$

where D is the residual square-sum obtained by subtracting the corrected reference spectrum from the sample spectrum. Moreover, the range Q for obtaining a sum for $x_k$ shows the baseline regions to the right and left of the carbon peak. Correction factors $a_1$, $a_2$, $a_3$ and $a_4$ included in Equation 3 can be calculated, for example, from the following condition which minimizes the residual square-sum by using the well-known least squares method.

$$\frac{\partial D}{\partial a_1} = 0, \ \frac{\partial D}{\partial a_2} = 0, \ \frac{\partial D}{\partial a_3} = 0, \ \frac{\partial D}{\partial a_4} = 0 \quad (5)$$

As means for determining a correction factor, a well-known technique such as the linear least-squares method or the nonlinear least-squares method may be appropriately used. In this way, in the method of measuring spectroscopic absorbance of the present invention, the correction factors $a_1$, $a_2$, $a_3$ and $a_4$ can be determined on the basis of the measured values of the sample spectrum and the reference spectrum.

At Step (S40) for calculating a differential spectrum, the values of $a_1$, $a_2$, $a_3$ and $a_4$ determined in the previous step are used to obtain a differential spectrum defined by the following equation.

$$A_S(x_k) - A_P(x_k) \quad (6)$$

Equation 4 represents a residual obtained by approximating the reference spectrum $A_R(X)$ to the sample spectrum $A_S(x)$, and further may represent a differential spectrum that shows the spectroscopic absorbance from only the measurement component.

Step (S50) for quantitative calculation is a step for quantifying the signal strength of the measurement component, for the purpose of quantitative determination, on the basis of the differential spectrum expressed with Equation (6). The numerical value of the signal strength may be a maximum value, may be an integrated intensity, or may be appropriately defined.

In the spectrometry method of the present invention, the steps, which are shown in FIG. 1 and described with Equations 1 to 5, are used to perform the correction calculation including the wave number shift correction, thereby making it possible to reduce unnecessary deformation, distortion and the like included in the baseline portion of the differential spectrum. Moreover, in the present invention, particularly in differential spectroscopy using FT-IR, by virtue of the minute wave number shift amount that is not greater than the resolution of the measuring equipment, it is possible to effectively remove spectroscopic absorbance of a background component in a wave number range that overlaps with a wave number range of minute spectroscopic absorbance of the measurement component. This can enhance sensitivity to the measurement component. In addition, the present invention can provide the data processing method as a computer program, thereby making it possible to automatically perform the correction calculation using a computer.

EXAMPLES

The present invention will be hereinafter described in detail using examples.

Example 1

Figure 3:
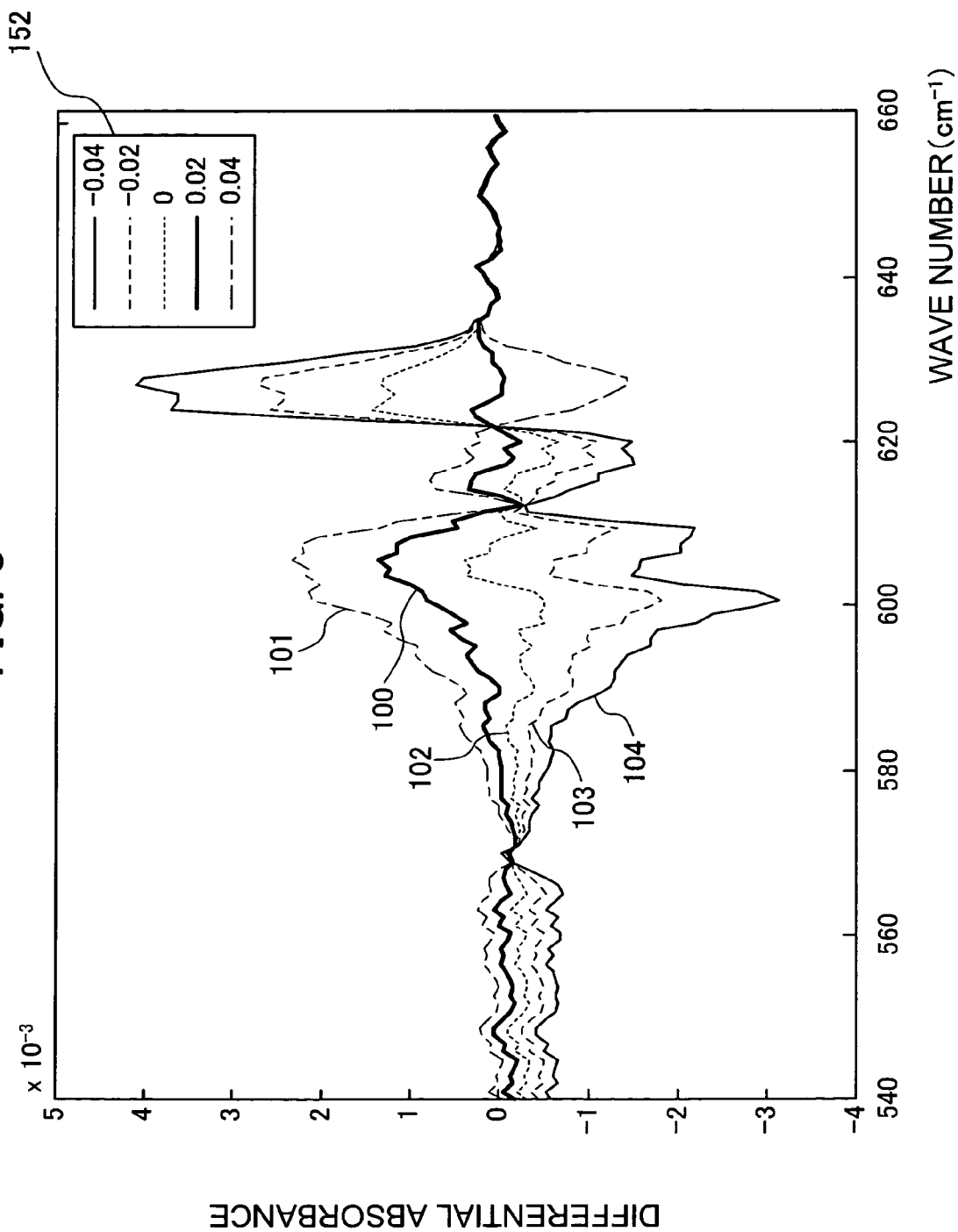
FIG. 3 is a diagram showing the wave number shift dependence of the differential spectrum of the present invention.

In Example 1, the wave number shift dependence of the differential spectrum in the method of the present invention is described. FIG. 3 is a diagram showing the wave number shift dependence of the differential spectrum, which is one embodiment of the present invention. As a reference sample, a substantially carbon-free CZ method silicon single crystal was used, and the range of wave numbers from 540 to 660 cm$^{-1}$ was measured at a wave number resolution of 1 cm$^{-1}$.

At first, an infrared spectroscopy spectrum (data R) of the reference sample was obtained, and an infrared spectroscopy spectrum (data S) of a measurement sample for quantitative determination of the concentration of substitutional carbon was obtained. Subsequently, by using a computer, $a_2$ of Equation 3 was assigned a certain constant value shifting the wave number of data R to thereby obtain an infrared spectroscopy spectrum (data R'). In addition, a differential spectrum (data D) was obtained by using the least squares method to determine values for $a_1$, $a_2$ and $a_4$ in Equation 3 such that Equation 4 is minimized when subtracting the data R' from the data S.

FIG. 3 shows a plurality of wave number shift values used for creating the data R', as a wave number shift amount 152 that is $a_2$ in Equation 3. Values of the wave number shift $a_2$ in the differential spectra 100, 101, 102, 103 and 104 are respectively 0.02, 0.04, 0, −0.02 and −0.04 [cm$^{-1}$].

Since it is well known that the infrared spectroscopy spectrum of the substitutional carbon exists at 605 cm$^{-1}$, the differential spectrum should ideally have a flat baseline and a spectral absorption component at 605 cm$^{-1}$. However, the wave number range of the absorbance due to phonon absorbance of the silicon overlaps with the wave number range of the absorbance of the substitutional carbon, and the differential spectrum obtained by subtracting the data R from the data S without using the wave number shift correction, i.e. the differential spectrum in cases where the wave number shift amount is 0, includes, as in the case of a differential spectrum 102, a baseline deformation around 625 cm$^{-1}$, which is greater than the spectral absorption of the substitutional carbon at 605 cm$^{-1}$. This deformation interferes with the determination of a very small amount of substitutional carbon in a silicon single crystal when using differential spectroscopy.

On the other hand, when observing differential spectra derived from reference spectra having wave numbers shifted by the infrared spectroscopy measuring method of the present invention (namely, the differential spectra 100, 101, 103 and 104), the intensity distribution of each of the differential spectra changed depending on the wave number shift amount 152. Particularly, with the conditions of the differential spectrum 100 (the wave number shift amount was 0.02 cm$^{-1}$), it was possible to essentially remove the baseline deviation that would result in the aforementioned deformation. Moreover, the peak height of the substitutional carbon at 605 cm$^{-1}$ also changed with a change in the wave number shift amount.

Example 2

Figure 4:
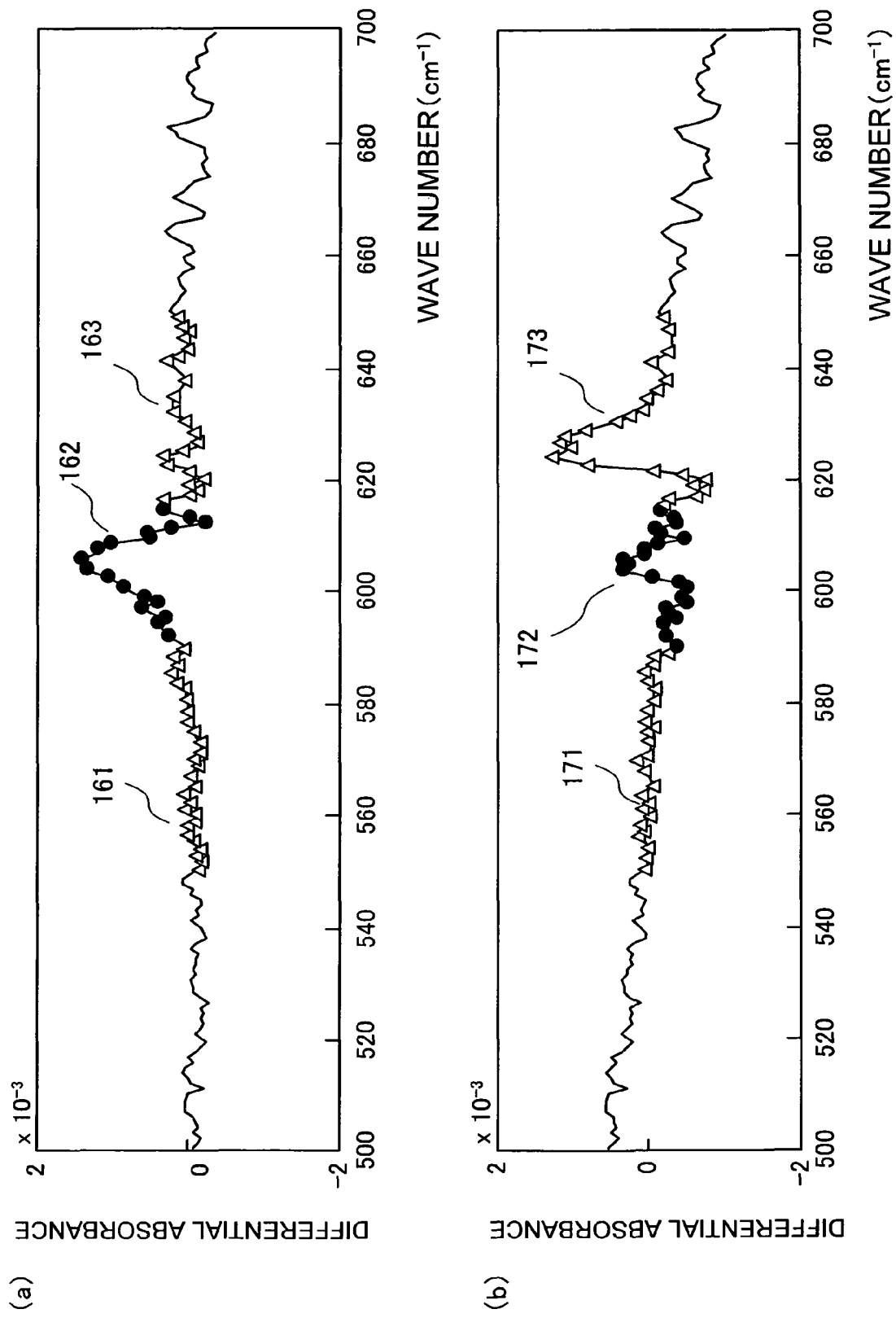
FIG. 4 is an FT-IR differential spectrum for quantitative determination of the substitutional carbon in the silicon single crystal, which is one embodiment of the present invention.

In Example 2, the differential spectrum after correction in the method of the present invention is described. FIG. 4(a) is a differential spectrum after FT-IR correction for quantitative determination of substitutional carbon in a silicon single crystal, which is one embodiment of the present invention. As for the FT-IR differential spectrum using the wave number shift correction in the present invention, the transverse axis is wave number [cm$^{-1}$], and the vertical axis is differential absorbance.

As described in Example 1, the method of calculating a differential spectrum is as follows. A reference spectrum obtained from a substantially carbon-free reference sample and a measurement spectrum obtained from a measurement sample for the quantitative determination of the concentration of substitutional carbon were measured. Subsequently, a wave number shift amount, which satisfies the condition to minimize the sum of squared residual, and a baseline offset amount were determined by use of the least squares method. A differential spectrum after correction was obtained from the determined wave number shift amount and the determined baseline offset amount. The reference spectrum before the wave number shift correction and the measurement spectrum were measured over the range of wave numbers from 500 to 700 cm$^{-1}$ at a wave number resolution of 1 cm$^{-1}$.

The differential spectrum after correction of FIG. 4(a) includes a low wave number region 161 in the range of wave numbers from 550 to 590 cm$^{-1}$, a high wave number region 163 in the range of wave numbers from 620 to 650 cm$^{-1}$, and a peak region 162 having an infrared absorption peak of the substitutional carbon in the range of wave numbers from 590 to 620 cm$^{-1}$, the region 161 and 163 being indicated by triangles, and the region 162 being indicated by closed circles in the diagram. Since, in FIG. 4(a), the deviation of the differential absorbance in the low wave number region 161 and the high wave number region 163 is smaller than the maximum value of the differential absorbance in the peak region 162, it is possible to clearly read the infrared absorption peak of the substitutional carbon of 605 cm$^{-1}$. The wave number shift amount for obtaining this differential spectrum after correction was 0.021 cm$^{-1}$, and was obtained by computational calculation using Equation 6.

FIG. 4(b) shows a differential spectrum obtained from the same reference sample and the same measurement sample, by using the prior art without the wave number shift. As for the FT-IR differential spectrum by the conventional method, the transverse axis is wave number [cm$^{-1}$] and the vertical axis is differential absorbance, as in the case of the aforementioned example. Only the correction for the subtraction factor and the baseline offset were used and that for the wave number shift was not used. The measurement conditions were the same as those used to generate the differential spectrum of FIG. 4(a).

Figure 7:
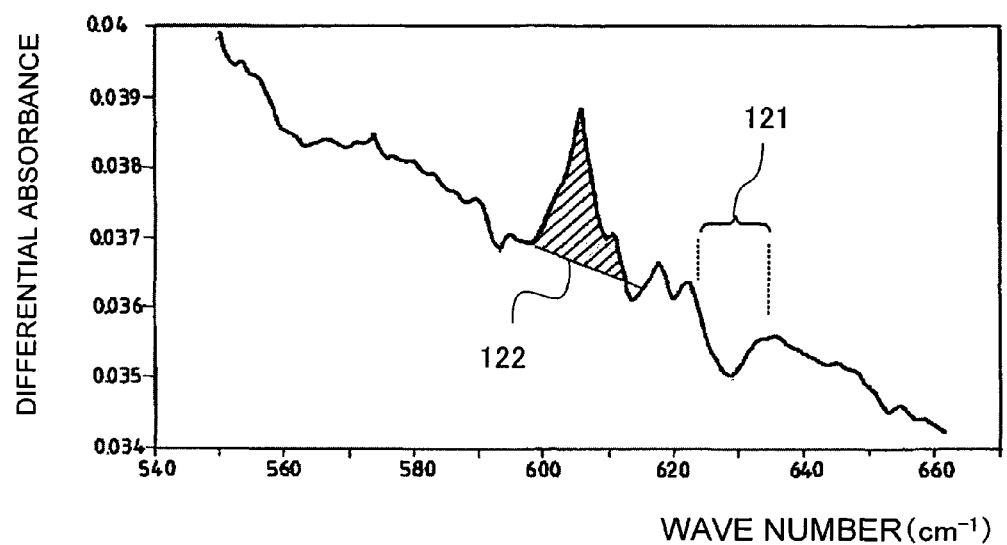
FIG. 7 is a diagram showing an example, in the prior art, of an infrared absorption spectrum of substitutional carbon in the method of obtaining an infrared absorption spectrum intensity of the substitutional carbon in a silicon single crystal using differential spectroscopy.

The differential spectrum after correction of FIG. 4(b) includes a low wave number region 171 in the range of wave numbers from 550 to 590 cm$^{-1}$, a high wave number domain 173 in the range of wave numbers from 620 to 650 cm$^{-1}$, and a peak region 172 having an infrared absorption peak of the substitutional carbon in the range of wave numbers from 590 to 620 cm$^{-1}$, the regions 171 and 173 being indicated by triangles, and the region 172 being indicated by closed circles in the diagram. As a result, in FIG. 4(b), deformation of the baseline remained in the high wave number region 173. This deformation results from phonon absorbance, as described above with reference to FIG. 3, as in the case of a distortion 121 at wave number 630 cm$^{-1}$ in FIG. 7 of the prior art. In this way, in FIG. 4(b), the deviation in the high wave number domain 173 is greater than the maximum value of the peak region 172 including the absorption peak of the substitutional carbon. Since peak components that are smaller than baseline deformation of a differential spectrum can be considered measurement errors, it is not possible to significantly identify the absorption peak of the substitutional carbon by the conventional method.

Example 3

Figure 5:
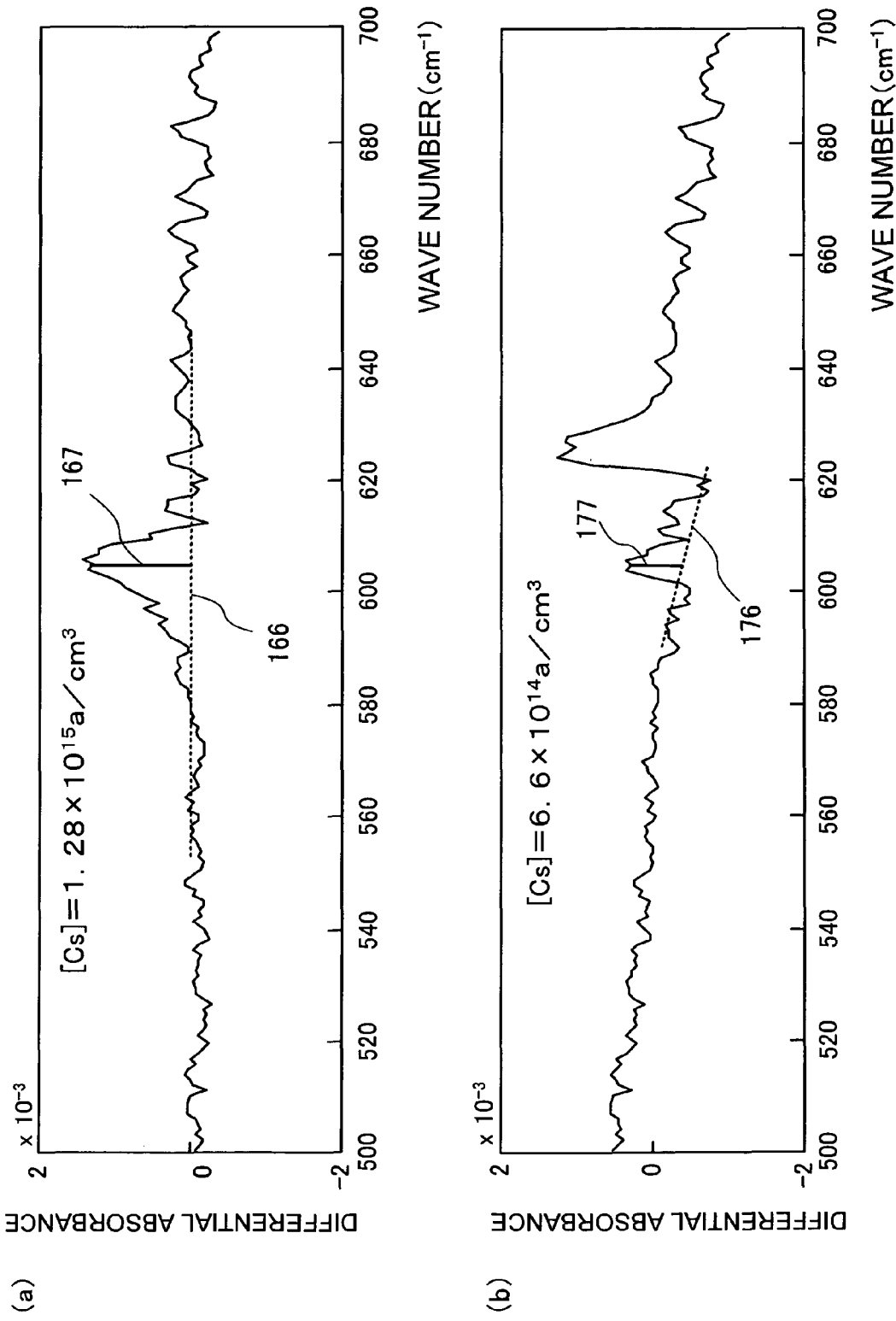
FIG. 5 shows an example for evaluating the signal-to-noise ratio of the differential spectrum after correction, which is one embodiment of the present invention.

In Example 3, the evaluation example of the detection limit in the method of the present invention is described. FIG. 5 is an example of evaluation by use of the concept of the signal-to-noise ratio (SN ratio), where the carbon peak height is a signal, and the data deviation in the right and left baseline region is noise, in a differential spectrum after correction which is one embodiment of the present invention. The actual measurement data was the same as the data of the aforementioned differential spectrum after correction in the present invention described with reference to FIG. 4 as well as the data of the differential spectrum in the conventional method, so the description of the overlapping portions will be omitted.

FIG. 5(a) is a differential spectrum after FT-IR correction for quantitative determination of substitutional carbon in a silicon single crystal. In this figure, the dotted line shows a baseline 166 for calculating a signal-to-noise ratio, and the solid line shows a peak height 167 from a point of maximum absorbance to the baseline at a wave number of 605 cm$^{-1}$.

The wave number region for calculating the noise indicating the data deviation of the baseline region were taken in the low wave number side (the range of 565 to 590 cm$^{-1}$) and the high wave number side (the range of 620 to 645 cm$^{-1}$) of the substitutional carbon absorption peak. From the actual measurements, the value of the peak height 167 was determined to be a differential absorbance of 0.00136 [Abs: unit of absorbance], the standard deviation of the differential absorbance in the low wave number region 161 and the high wave number region 163 was determined to be 0.000114 [Abs], and the signal-to-noise ratio obtained by dividing the peak height 167 by the standard deviation was determined to be 11.9. Moreover, from the peak height, the concentration of the substitutional carbon included in the measurement sample was determined to be 1.28×10$^{15}$ a/cm3.

In addition, the detection limit, assumed to be 3 times the standard deviation of the noise, was estimated to be approximately 3.00×10$^{14}$ a/cm$^3$. This detection limit is approximately 1/15 of the detection limit for the substitutional carbon in Patent Document 1 being approximately 4.5×10$^{15}$ a/cm$^3$ (0.09 [ppma]). That is to say, in the method of the present invention, it is even possible to quantitatively measure the concentration of a very small amount of substitutional carbon, the amount being one order of magnitude smaller than that of the prior art.

FIG. 5(b) is an FT-IR differential spectrum for quantitative determination of the substitutional carbon in the silicon single crystal in the conventional method. In this figure, the dotted line shows a baseline 176, and the solid line shows a peak height 177 from a point of maximum absorbance to the baseline at a wave number of 605 cm$^{-1}$. In the differential spectrum according to the conventional method, the baseline deformation is greater in the high wave number region, as described above with reference to FIG. 5(b). Accordingly, the baseline 176 for calculating a signal-to-noise ratio needs to be expediently defined so as to be able to find an absorption peak, and is specifically defined as a straight line passing between points on the spectrum at wave number 595 cm$^{-1}$ and wave number 615 cm$^{-1}$.

The wave number region for calculating noise was set as in the case of FIG. 5(a). The value of the peak height 177 was determined to be a differential absorbance of 0.0007 [Abs], the standard deviation of the differential absorbance of the points of measurement included in the low wave number region 171 and the high wave number region 173 was determined to be 0.000404 [Abs], and the signal-to-noise ratio obtained by dividing the peak height 177 by the standard deviation was determined to be 1.75.

Moreover, the concentration of the substitutional carbon included in this measurement sample was determined to be $6.6 \times 10^{14}$ a/cm$^3$. However, the peak height 177 in the conventional method is lower than the peak height 167 in the present invention, and the baseline deviation is greater than the absorption peak of the substitutional carbon in the differential spectrum in the conventional method. Accordingly, in the conventional method, the intensity of the absorption peak of the substitutional carbon is lower than that of the noise, and quantitatively is not assured.

From these results, as a sensitivity improvement, the SN ratio of the infrared spectroscopy of the present invention reached approximately 6 times that of the conventional method. Moreover, the detection limit of substitutional carbon in the present invention was decreased to a very small amount, being approximately 1/15 of that of the measurement example of the conventional method.

Example 4

Example 4 shows that the infrared absorption peak of the substitutional carbon in the infrared spectroscopy of the present invention is approximated by a computation model.

Figure 6:
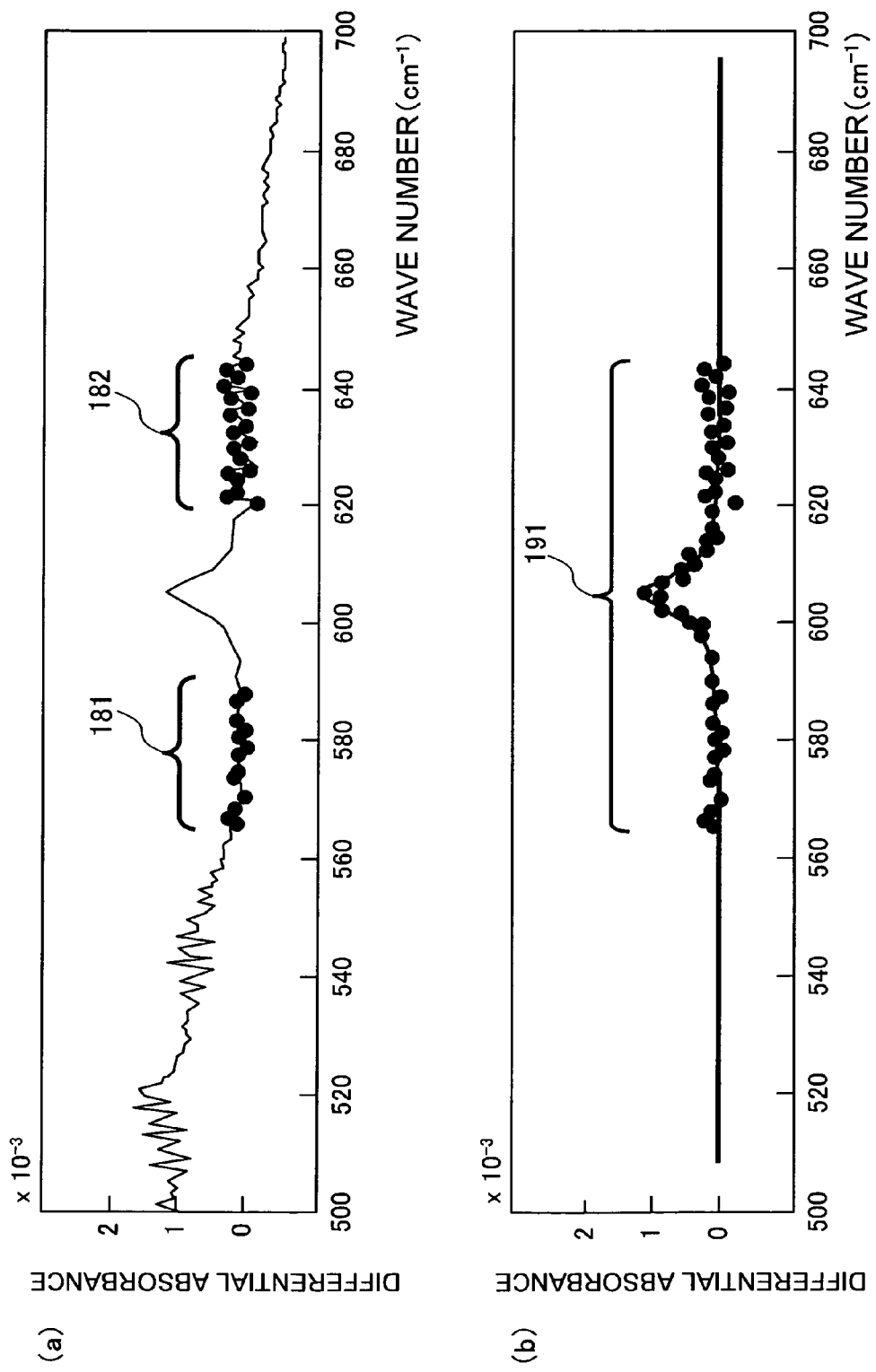
FIG. 6 is a diagram showing an infrared absorption spectrum of the substitutional carbon fitted with a Lorentzian line shape, which is one embodiment of the present invention.

FIG. 6 is a diagram showing an infrared absorption spectrum of the substitutional carbon for peak-fitting using a Lorentzian peak shape.

FIG. 6(a) is a diagram showing the low wave number side (a region 181 of 565 to 590 cm$^{-1}$) and the high wave number side (a region 182 of 620 to 645 cm$^{-1}$) of substitutional carbon absorption peak, which are considered noise, and which have been used in the explanation of the above-mentioned detection limit. FIG. 6(b) is a diagram showing points of measurement in a fitting process for minimizing the sum of squared residual with the actual measurement, on the assumption that the entire infrared absorption spectrum of the substitutional carbon is an absorption spectrum that has a Lorentzian peak shape. Measured data points in the range of wave numbers from 565 to 645 cm$^{-1}$ including the infrared absorption peak of the substitutional carbon were used for the fitting. An absorption line peak shape in relation to the infrared absorption peak of the substitutional carbon can be expressed, for example, by the following equation;

$$A_P(x_k) - a_1 A_R(x_k - a_2) + a_3 + a_4 x_k + a_5 L(x_k, a_6, a_7) \quad (7)$$

where $a_5$ is peak intensity, $a_6$ is a peaks-centered wave number, $a_7$ is full width at half maximum height, and $L(x_k, a_6, a_7)$ is a normalized Lorentzian peak shape. The Lorentzian peak shape is expressed by the following equation.

$$L(x_k, a_6, a_7) = \frac{a_7^2}{(x_k - a_6)^2 + a_7^2} \quad (8)$$

As for the calculation of factors $a_1$ to $a_7$, linear least-squares method or nonlinear least-squares method may be used as in the case of the calculation of the correction factor using the aforementioned Equations 5 and 6. Specifically, as for the absorption spectrum having an intensity and a full width at the half maximum height of the substitutional carbon around the wave number 605 cm$^{-1}$, it is possible to obtain a Lorentzian line shape fitted to the measured data points in the range 191 of wave numbers from 565 to 645 cm$^{-1}$, and the result is shown with the solid line in FIG. 6(b). Moreover, the obtained wave number shift was 0.0206 cm$^{-1}$, the peak position was 604.92 cm$^{-1}$, and the full width at the half maximum height was 3.14 cm$^{-1}$.

The spectroscopic absorbance measurement method and the spectroscopic absorbance measurement apparatus of the present invention can be used, for example, in measurement of an impurity concentration in a silicon single crystal or the like.

What is claimed is:

1. A method of measuring spectroscopic absorbance, in differential spectroscopy, for obtaining only a spectroscopic absorption spectrum of a measurement component from a sample spectrum of a measurement sample and from a reference spectrum of a reference sample, the sample spectrum having spectroscopic absorbance of a background component in a frequency domain of spectroscopic absorbance of the measurement component and in a frequency domain overlapping with the spectroscopic absorbance of the measurement component, and the reference spectrum substantially not including the measurement component but having the spectroscopic absorbance of the background component, wherein, when a differential spectrum is obtained, correction is performed including a frequency shift to any one of the sample spectrum or the reference spectrum in order to remove the spectroscopic absorbance of the background component.

2. A method of measuring spectroscopic absorbance, in differential spectroscopy, for obtaining only a spectroscopic absorption spectrum of a measurement component from a sample spectrum of a measurement sample and from a reference spectrum of a reference sample, the sample spectrum having spectroscopic absorbance of a background component in a frequency domain of spectroscopic absorbance of the measurement component and in a frequency domain overlapping with the spectroscopic absorbance of the measurement component, and the reference spectrum not substantially including the measurement component but having the spectroscopic absorbance of the background component, wherein, when a differential spectrum is obtained, correction is performed including a frequency shift to any one of the sample spectrum or the reference spectrum in order to substantially flatten the baseline.

3. The method of measuring spectroscopic absorbance according to claim 1, wherein an amount of the frequency shift is not greater than frequency resolution of the spectroscopic absorbance measurement.

4. The method of measuring spectroscopic absorbance according to claim 1, wherein the method of measuring spectroscopic absorbance is FT-IR (Fourier transformation infrared spectroscopy), the measurement component is an impurity in a silicon single crystal, and concentration of the impurity is determined from a spectroscopic absorbance peak height of the measurement component in the differential spectrum.

5. The method of measuring spectroscopic absorbance according to claim 4, wherein the impurity is substitutional carbon.

6. A computer program on a non-transitory computer readable medium, to cause a computer to perform the steps of:

storing a sample spectrum having spectroscopic absorbance of the measurement component and a background component in a frequency domain overlapping with the spectroscopic absorbance of the measurement component;

storing a reference spectrum substantially not including the measurement component but having the spectroscopic absorbance of the background component;

removing the spectroscopic absorbance of the background component by correction including a frequency shift to any one of the sample spectrum or the reference spectrum, and calculating a correction factor for flattening a baseline of the spectroscopic absorbance of the measurement component; and calculating a differential spectrum of the sample spectrum and the reference spectrum by using the correction factor.

7. An apparatus for measuring spectroscopic absorbance, comprising:

a first device configured to store a sample spectrum having spectroscopic absorbance of the measurement component and a background component in a frequency domain overlapping with the spectroscopic absorbance of the measurement component;

a second device configured to store a reference spectrum substantially not including the measurement component but having the spectroscopic absorbance of the background component; and a device configured to calculate a differential spectrum of the sample spectrum and the reference spectrum, wherein, the device configured to calculate the differential spectrum performs correction including a frequency shift to any one of the sample spectrum or the reference spectrum in order to remove the spectroscopic absorbance of the background component.

* * * * *